(12) United States Patent
Wang et al.

(10) Patent No.: US 10,064,802 B2
(45) Date of Patent: Sep. 4, 2018

(54) ORAL COMPOSITIONS, DENTAL STRUCTURES AND METHODS OF DELIVERING ORAL COMPOSITIONS

(71) Applicant: 3M INNOVATIVE PROPERTIES COMPANY, St. Paul, MN (US)

(72) Inventors: Yizhong Wang, Woodbury, MN (US); Joel D. Oxman, Minneapolis, MN (US); Paul R. Klaiber, Mahtomedi, MN (US); Jie J. Liu, Woodbury, MN (US); Joanne A. Fitch, Oakdale, MN (US); Tiffany T. Ton, Woodbury, MN (US); Reinhold Hecht, Kaufering (DE)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 0 days.

(21) Appl. No.: 14/917,431

(22) PCT Filed: Sep. 10, 2014

(86) PCT No.: PCT/US2014/054901
§ 371 (c)(1),
(2) Date: Mar. 8, 2016

(87) PCT Pub. No.: WO2015/038580
PCT Pub. Date: Mar. 19, 2015

(65) Prior Publication Data
US 2016/0220473 A1    Aug. 4, 2016

Related U.S. Application Data

(60) Provisional application No. 61/876,599, filed on Sep. 11, 2013, provisional application No. 61/876,435, filed on Sep. 11, 2013, provisional application No. 61/876,602, filed on Sep. 11, 2013, provisional application No. 61/876,606, filed on Sep. 11, 2013.

(51) Int. Cl.
*A61K 8/81* (2006.01)
*A61Q 11/00* (2006.01)

(52) U.S. Cl.
CPC .......... *A61K 8/8147* (2013.01); *A61K 8/8152* (2013.01); *A61Q 11/00* (2013.01); *A61K 2800/5424* (2013.01); *A61K 2800/594* (2013.01); *A61K 2800/92* (2013.01)

(58) Field of Classification Search
None
See application file for complete search history.

(56) References Cited

U.S. PATENT DOCUMENTS

| | | |
|---|---|---|
| 4,134,935 A | 1/1979 | Quiring |
| 4,883,534 A | 11/1989 | Sandham |
| 5,160,737 A | 11/1992 | Friedman |
| 5,330,746 A | 7/1994 | Friedman |
| 5,438,076 A | 8/1995 | Friedman |
| 5,639,795 A | 6/1997 | Friedman |
| 5,776,435 A | 7/1998 | Gaffar |
| 6,177,097 B1 | 1/2001 | Hanke |
| 6,197,331 B1 | 3/2001 | Lerner |
| 6,485,709 B2 | 11/2002 | Banerjee |
| 6,770,266 B2 | 8/2004 | Santarpia, III |
| 6,854,973 B2 | 2/2005 | Butcher |
| 2003/0183124 A1 | 10/2003 | Engelbrecht |
| 2004/0126333 A1 | 7/2004 | Galli |
| 2004/0136927 A1* | 7/2004 | Kim ............... A61C 19/066 424/53 |
| 2004/0258723 A1* | 12/2004 | Singh ............. A61C 19/063 424/401 |
| 2005/0063921 A1 | 3/2005 | Charmot |
| 2005/0113510 A1 | 5/2005 | Feldstein |
| 2005/0196358 A1 | 9/2005 | Georgiades |
| 2005/0215727 A1 | 9/2005 | Feldstein |
| 2006/0004120 A1 | 1/2006 | Orlowski |
| 2006/0024246 A1 | 2/2006 | Maitra |
| 2006/0171906 A1* | 8/2006 | Singh ............. A61K 8/0208 424/53 |
| 2008/0299520 A1 | 12/2008 | Ali |
| 2009/0191279 A1 | 7/2009 | Kennard |
| 2009/0257961 A1 | 10/2009 | Deng |
| 2009/0324516 A1 | 12/2009 | Muscle |

(Continued)

FOREIGN PATENT DOCUMENTS

| | | |
|---|---|---|
| EP | 0404558 | 12/1990 |
| JP | 61-289006 | 12/1986 |
| WO | WO 1994-04126 | 3/1994 |
| WO | WO 2009-150596 | 12/2009 |
| WO | WO 2011-084673 | 7/2011 |
| WO | WO 2011-162965 | 12/2011 |
| WO | WO 2013-162404 | 10/2013 |
| WO | WO 2015-038376 | 3/2015 |
| WO | WO 2015-038400 | 3/2015 |
| WO | WO 2015-071386 | 5/2015 |
| WO | WO 2015-160762 | 10/2015 |

OTHER PUBLICATIONS

Jonier, "The bleaching of teeth: A review of literature". Journal of Dentistry, Aug. 2006, vol. 34, No. 7, pp. 412-419.
International Search Report for PCT International Application No. PCT/US2014/054901 dated Feb. 5, 2015, 3 pages.

*Primary Examiner* — Brian M Gulledge

(57) ABSTRACT

An oral composition and a method of delivering an oral composition to a dental structure are described. The oral composition can include a solvent; an acidic copolymer having acidic acrylate monomeric units, acidic methacrylate monomeric units, or a combination thereof; a neutral copolymer having neutral acrylate monomeric units, neutral methacrylate monomeric units, or a combination thereof; and optionally an active agent. The acidic and neutral copolymers can be dissolved in the oral composition and the oral composition can form a film on a surface when contacted with an aqueous solution.

16 Claims, 1 Drawing Sheet

(56) References Cited

U.S. PATENT DOCUMENTS

2011/0250557 A1  10/2011  Qian
2013/0052146 A1   2/2013  Yang

* cited by examiner

ORAL COMPOSITIONS, DENTAL STRUCTURES AND METHODS OF DELIVERING ORAL COMPOSITIONS

CROSS REFERENCE TO RELATED APPLICATIONS

This application claims the benefit of U.S. Provisional Application Nos. 61/876,599, 61/876,435, 61/876,602 and 61/876,606 filed Sep. 11, 2013, which is incorporated herein by reference in its entirety.

FIELD

The present disclosure generally relates to oral compositions, e.g. aqueous or nonaqueous oral coating compositions, and methods of delivering oral compositions. Some aspects of this disclosure generally relate to dental structures.

BACKGROUND

Preventive actives-based oral materials, such as dental sealants, varnishes, gels, tooth pastes, oral rinse, and extended contact varnishes, have been used to release various amounts of active agents (e.g., fluoride, calcium and phosphate ions, anti-sensitive agents, antimicrobial agents, and biofilm disruptors) via different delivery vehicles to provide potential uptake or bioactivity into oral tissues. These materials utilize several different application techniques and are suitable for different patients. For example, sealants and extended contact varnishes typically require curing to provide crosslinking for extended durability and retention. Alternatively, fluoride rinses and gels provide simplified delivery of fluoride.

Dental articles are used for treatment of a variety of dental maladies. Dental articles have been used to deliver oral active agents. Preventive actives-based oral materials, such as dental sealants, varnishes, gels, tooth pastes, oral rinse, and extended contact varnishes, have been used to release various amounts of active agents (e.g., fluoride, calcium and phosphate ions, anti-sensitive agents, antimicrobial agents, and biofilm disruptors) via different delivery vehicles to provide potential uptake or bioactivity into oral tissues. These materials utilize several different application techniques and are suitable for different patients. For example, sealants and extended contact varnishes typically require curing to provide crosslinking for extended durability and retention. Alternatively, fluoride rinses and gels provide simplified delivery of fluoride.

SUMMARY

Existing preventive actives-based dental materials generally fall into two categories: a) crosslinked/cured materials (e.g. dental sealants and extended contact varnishes), that are durable and "semi-permanent to permanent;" and b) temporary coating materials (e.g. varnishes and gels), that can be applied or dried to provide a weak, non durable, sticky coating. Such coating materials are generally applied to dental tissues for 5-10 minute and can be rinsed from the dental tissues. Crosslinked/cured materials are durable, but typically require chemical curing to provide crosslinking for extended durability and retention. Some methods of using existing preventive actives-based dental materials require complicated procedures with limited initial release of active agents. In addition, the released active concentration of some existing preventive actives-based dental materials is low and the contact time between tooth structure and such dental materials is short.

Hydrophobic coating materials are recently used for hypersensitivity reduction and fluoride treatment. These hydrophobic coating materials in general are made from tree rosin and derivates thereof. Tree rosin and its derivatives need organic solvents such as the mixtures of hexane and ethanol to dissolve. After application onto the dental tissues, the non-aqueous solvent such as ethanol and hexane, slowly evaporate to form a soft and sticky hydrophobic coating. The resulted hydrophobic coating has an undesirable hexane odor, contains small bubbles due to the evaporation of hexane, and exhibits a rough intraoral surface sensation. When theses existing hydrophobic coating materials are used to deliver active agents, the bioavailability and uptake of active agents from these hydrophobic coating materials is relative low and ineffective because the active agents are dispersed in organic solvent and hydrophobic rosin, resulting in a slow ion transport and release. In addition, when the soft and sticky hydrophobic coating contacts hot drink or food, the coating can be worn out very easily, and most of the active agents are ingested in a person's stomach before they deposit on the dental tissues.

The present disclosure generally relates to oral compositions, methods of delivering oral compositions and dental structures. Generally, the oral composition, methods and dental structures of the present disclosure, can provide enhanced release of active agents (medicaments), more efficient bioactivity and improved ease of application. The oral composition of the present disclosure can resist brush abrasion, but does not require on-web chemical curing. Further, the oral composition of the present disclosure can form a film in less than about 30 seconds after the oral composition is contacted with water or dried with a stream of compressed air. In addition, the oral composition and methods of the present disclosure can provide coatings that seal open dentin tubules and/or enamel cracks to minimize tooth sensitivity.

Some aspects of the present disclosure provide an oral composition. The oral composition can include a solvent comprising water and a cosolvent chosen from lower alkyl alcohols, acetone and a combination thereof; an acidic copolymer comprising acidic acrylate monomeric units, acidic methacrylate monomeric units, or a combination thereof; a neutral copolymer comprising neutral acrylate monomeric units, neutral methacrylate monomeric units, or a combination thereof; and optionally an active agent. The oral composition can include from about 6 to about 18 wt-% of water, from about 30 to about 80 wt-% of cosolvent, from about 15 to about 50 wt-% of sum of the acidic and neutral copolymers, and the wt-% of each component is based on the total weight of the composition. The acidic and neutral copolymers can be dissolved in the oral composition and the oral composition can form a film on a surface when contacted with an aqueous solution.

Some aspects of the present disclosure provide an oral composition. The oral composition can include a solvent chosen from lower alkyl alcohols, THF, DMSO, ionic liquid, TEC, ethyl acetate, acetone, and a combination thereof; an acidic copolymer comprising acidic acrylate monomeric units, acidic methacrylate monomeric units, or a combination thereof; a neutral copolymer comprising neutral acrylate monomeric units, neutral methacrylate monomeric units, or a combination thereof; and optionally an active agent. The oral composition can include from about 30 to about 80 wt-% of solvent, from about 15 to about 50 wt-% of sum of the acidic and neutral copolymers, and the wt-% of each component is based on the total weight of the composition. The acidic and neutral copolymers can be dissolved in the oral composition and the oral composition is capable of forming a film on a surface when contacted with an aqueous solution.

Some aspects of the present disclosure provide an oral composition. The oral composition can include a solvent comprising water and a cosolvent chosen from lower alkyl alcohols, acetone and a combination thereof; an acidic copolymer chosen from Eudragit S100, Eudragit L100, Eudragit L100-55, AC210 and combinations thereof; a neutral copolymer chosen from Eudragit RS100 and Eudragit RL 100; Eudragit E100; and optionally a fluoride salt. The oral composition can include from about 8 to about 12 wt-% of water, from about 30 to about 80 wt-% of cosolvent, from about 15 to about 50 wt-% of sum of the acidic and neutral copolymers. The acidic and neutral copolymers can be dissolved in the oral composition and the oral composition can form a film on a surface when contacted with an aqueous solution.

Some aspects of the present disclosure provide a method of delivering an oral composition to a dental structure. The method can include providing an oral composition; applying the oral composition to the dental structure; and contacting the oral composition with an aqueous solution, thereby forming a polymeric film on the dental structure.

Some aspects of the present disclosure provide a dental structure. The dental structure can include a dental article, and a film on a surface of the dental article. The film can be formed by contacting an oral composition with an aqueous solution or by drying the oral composition on the dental article. The oral composition can include an acidic copolymer comprising acidic acrylate monomeric units, acidic methacrylate monomeric units, or a combination thereof; a neutral copolymer comprising neutral acrylate monomeric units, neutral methacrylate monomeric units, or a combination thereof; and optionally an active agent.

Other features and aspects of the present disclosure will become apparent by consideration of the detailed description and accompanying drawings.

DETAILED DESCRIPTION

Figure 1:
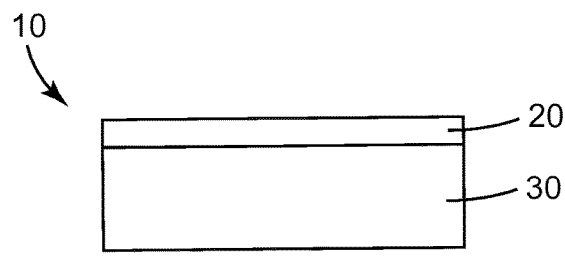
FIG. 1 is a schematic side view of a dental structure according to an embodiment of the invention.
Figure 2:
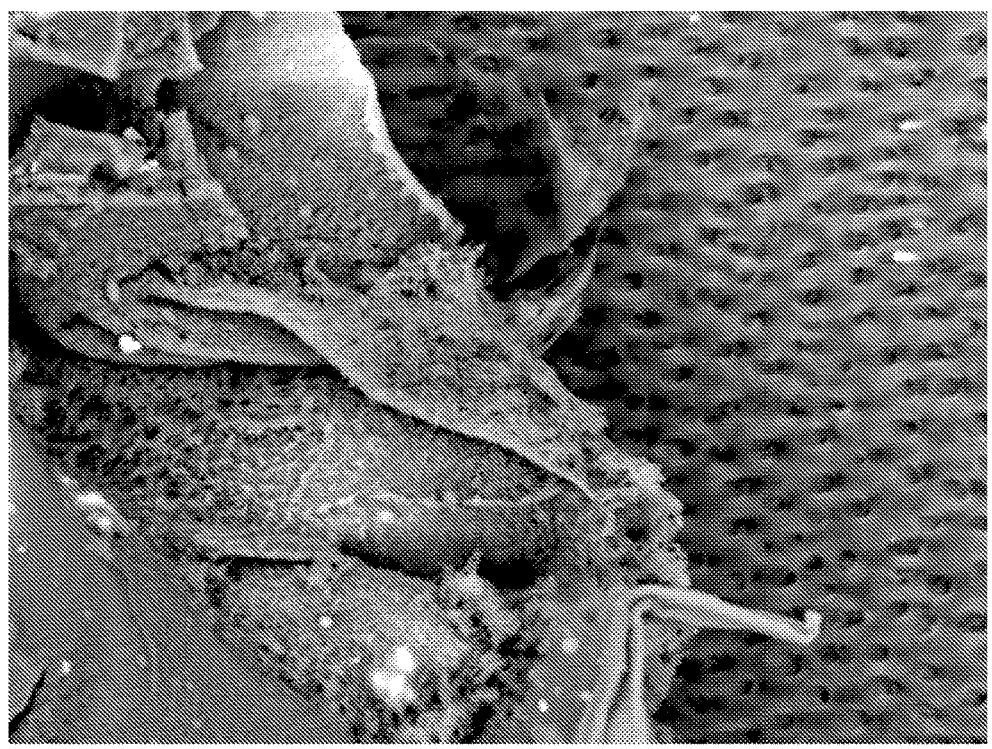
FIG. 2 is a SEM Image of Coated and Uncoated Bovine Dentin.

Before any embodiments of the present disclosure are explained in detail, it is understood that the invention is not limited in its application to the details of use, construction, and the arrangement of components set forth in the following description or illustrated in the following drawings. The invention is capable of other embodiments and of being practiced or of being carried out in various ways that will become apparent to a person of ordinary skill in the art upon reading the present disclosure. Also, it is understood that the phraseology and terminology used herein is for the purpose of description and should not be regarded as limiting. The use of "including," "comprising," or "having" and variations thereof herein is meant to encompass the items listed thereafter and equivalents thereof as well as additional items. It is understood that other embodiments may be utilized and structural or logical changes may be made without departing from the scope of the present disclosure.

The present disclosure generally relates to methods of delivering oral compositions and methods of delivering an active agent to dental structures. Particularly, for example, the methods of the present disclosure can provide a more effective use of active agents, a better adhesion to dental structures, more durable coatings, a faster ion transport and release, and a non sticky, smooth feeling on dental structures.

As used herein, dental structures include, but are not limited to, dental tissues and dental articles.

As used herein, dental tissues include, but are not limited to hard and soft dental tissues. Hard and soft oral tissues include, but are not limited to, teeth, dental arch, and the surrounding tissues and support structures including gingiva and hard palate.

As used herein, dental articles include, but are not limited to an article that can be attached (e.g., bonded) to dental tissues (e.g., a tooth structure). Examples of dental articles include, but are not limited to, replacements, inlays, onlays, veneers, full and partial crowns, bridges, implants, implant abutments, copings, dentures, posts, bridge frameworks and other bridge structures, abutments, orthodontic appliances and devices including, but not limited to archwires, buccal tubes, brackets and bands, and prostheses (e.g., partial or full dentures).

In some embodiments, the oral composition of the present disclosure can include a solvent, an acidic copolymer, a neutral copolymer and optionally an active agent.

Solvents

In certain embodiments, the solvent can include water and a cosolvent. In such certain embodiments, the oral composition of the present disclosure is an aqueous oral composition. In some of these certain embodiments, the oral composition comprises from about 6 to about 18 wt-% of water. In some of these certain embodiments, the oral composition comprises from about 8 to about 12 wt-% of water. The cosolvent can be chosen from lower alkyl alcohols and acetone. As referred to herein, the lower alkyl alcohols can include low carbon number (e.g. $C_1$-$C_5$) alcohols. Examples of lower alkyl alcohols as used herein include, but are not limited to, ethanol, isopropanol, propylene glycol, glycerin and low molecular weight polyethylene glycol and ethylene glycol based ester alcohols. In some of these certain embodiments, the cosolvent can be ethanol. In some other embodiments, the oral composition comprises from about 30 to about 80 wt-% of cosolvent. In some of these certain embodiments, the oral composition comprises from about 45 to about 60 wt-% of the cosolvent.

In other embodiments, the solvent can be chosen from lower alkyl alcohols, tetrahydrofuran (THF), dimethyl sulfoxide (DMSO), ionic liquid (e.g., tris(2-hydroxyethyl)-methyl ammonium methylsulfate), triethyl citrate (TEC), ethyl acetate, acetone, and a combination thereof. In such other embodiments, the oral composition of the present disclosure is a non aqueous oral composition. In some of these other embodiments, the solvent can be ethanol. In some of these other embodiments, the oral composition comprises from about 30 to about 80 wt-% of solvent. In some of these other embodiments, the oral composition comprises from about 45 to about 60 wt-% of the solvent.

In any of above embodiments, the solvent can further include at least one additional component chosen from isopropanol, propylene glycol, glycerin, low molecular weight polyethylene glycol, ethylene glycol based ester alcohols, and combinations thereof.

Acidic Copolymer

Acidic copolymers can, for example, lower the pH of the oral composition. As a result, acidic copolymers can be used as film formers. When the film is formed, it can, for example, provide an anchoring structure to dental structures and promote such tissues to enhance uptake active agents.

In some embodiments, the acidic copolymer can include, but is not limited to, an acidic acrylic copolymer of a monomeric unit selected from the group consisting of acrylic acid, methacrylic acid and combinations thereof.

In some embodiments, the acidic copolymer can include a copolymer of methacrylic acid and methyl methacrylate. In some other embodiments, the acidic copolymer can include Eudragit® S100 (marketed by Evonic Industries AG, Damstadt, Germany), Eudragit® L100 (marketed by Evonic Industries AG, Damstadt, Germany), Eudragit® L100-55 (marketed by Evonic Industries AG, Damstadt, Germany), AC210 (marketed by The Lubrizol Corporation, Wickliffe, Ohio, USA), or combinations thereof. In some embodiments, the molecular weight of the acidic copolymer can be from about 5,000 to about 500,000. In other embodiments, the molecular weight of the neutral copolymer can be from about 10,000 to about 100,000.

Neutral Copolymers

In some embodiments, the neutral acrylate monomeric units can include, but are not limited to, isobutyl acrylate, tert-butyl acrylate, 2-ethylhexyl acrylate, lauryl acrylate, lauryl/tridecyl acrylate, cetyl acrylate, stearyl acrylate, cyclohexyl acrylate, benzyl acrylate, isobornyl acrylate, 2-methoxyethyl acrylate, 2-ethoxyethyl acrylate, 2-ethoxyethoxyethyl, acrylate, 2-phenoxyethyl acrylate, tetrahydrofurfuryl acrylate, 2-hydroxyethyl acrylate, 2-hydroxypropyl acrylate, 4-hydroxybutyl acrylate, 1,4-butanediol acrylate, and combinations thereof. In some other embodiments, diacrylates can include the diacrylates of: 1,4-butanediol, 1,6-hexanediol, tetraethylene glycol, tripropylene glycol, and ethoxylated bisphenol-A. In other embodiments, triacrylate monomers include those of: trimethylol propane, ethoxylated, glyceryl propoxy, and pentaerythritol.

In some embodiments, neutral methacrylate monomeric units can include, but are not limited to, methyl methacrylate, ethyl methacrylate, n-butyl methacrylate, isobutyl methacrylate, tert-butyl methacrylate, 2-ethylhexyl methacrylate, lauryl methacrylate, alkyl methacrylate, tridecyl methacrylate, stearyl methacrylate, cyclohexyl methacrylate, benzyl methacrylate, isobornyl methacrylate, 2-hydroxyethyl methacrylate, 2-hydroxypropyl methacrylate, dimethylaminoethyl methacrylate, diethylaminoethyl methacrylate, glycidyl methacrylate, tetrahydrofurfuryl methacrylate, allyl methacrylate, ethylene glycol methacrylate, triethylene glycol methacrylate, tetraethylene glycol methacrylate, 1,3-butyleneglycol methacrylate, 1,6-hexanediol methacrylate, trimethylopropane methacrylate, ethoxyethyl methacrylate and trifluoroethyl methacrylate, and combinations thereof.

In some embodiments, the neutral copolymer can include copolymers of ethyl acrylate, methyl methacrylate and methacrylic acid ester with quaternary ammonium groups.

In some embodiments, the neutral copolymer can include Eudragit RS100 (marketed by Evonic Industries AG, Damstadt, Germany), Eudragit RL 100 (marketed by Evonic Industries AG, Damstadt, Germany), and combinations thereof.

Neutral copolymers can be used as film formers with a flexible property and a low strength that maintain adhesion during scratching or tooth brushing. However, neutral copolymers have poor solubility in water and/or alcohol based coating system. The acidic copolymer can, for example, help to dissolve the neutral copolymers in solvents system and the flexible neutral copolymers can help to form a tougher film and thus provide a good adhesion to dental structures. In some embodiments, the consistency of the oral composition of the present disclosure can be from about 45 to about 110. The viscosities of the oral composition are characterized with consistency. The higher the consistency of the composition represents the easier spreading of the composition when pressure is applied, which means lower viscosity. The oral composition has certain consistency range to be applied in an oral cavity. When the consistency of the oral composition is too high, the oral composition is too runny and produces a dripping problem. When the consistency of the oral composition is too low, the oral composition is too viscous and is difficult to spread.

In some embodiments, the molecular weight of the neutral copolymer can be from about 10,000 to about 100,000.

In some embodiments, the oral composition can comprise from about 15 to about 50 wt-% of sum of the acidic and neutral copolymers. The wt-% of each component of the present disclosure is based on the total weight of the composition. In some other embodiments, the oral composition can comprise from about 20 to about 48 wt-% of sum of the acidic and neutral copolymers. In other embodiments, the oral composition can comprise from about 22 to about 37 wt-% of sum of the acidic and neutral copolymers.

Basic Copolymer

In some embodiments, the oral composition used in the methods of the present disclosure can further include a basic copolymer having basic acrylate monomeric units, basic methacrylate monomeric units, or a combination thereof. The basic copolymer, for example, can be used to crosslink the acidic polymer by ionic interaction to improve mechanical properties of the oral composition of the present disclosure.

In some embodiments, the basic copolymer can include a copolymer containing dimethylaminoethyl methacrylate. In some other embodiments, the basic copolymer can include a copolymer based on dimethylaminoethyl methacrylate, butyl methacrylate, and methyl methacrylate. In other embodiments, the basic copolymer can be chosen from Eudragit E100 and other copolymer containing dimethylaminoethyl methacrylate for ionic crosslinking.

In some embodiments, the molecular weight of the basic copolymer can be from about 10,000 to about 100,000. In some other embodiments, the oral composition comprises from about 0 to about 1.0 wt-% of the basic copolymer. In other embodiments, the oral composition comprises from about 0.1 to about 0.4 wt-% of the basic copolymer.

In some embodiments, the weight ratio of the basic copolymer to the acidic polymer can be from about 0 to about 1:10. In other embodiments, the weight ratio of the basic copolymer to the acidic polymer can be from about 1:100 to about 1:15. Such weight ratio, for example, can provide a good ionic cross-linking. When the weight ratio of the basic copolymer to the acidic polymer is too high, the interaction between the basic copolymer and the acidic polymer is too strong. As a result, the two copolymers form very high viscosity gels that cannot dissolve in the oral composition system and is very difficult to handle and mix. Such oral composition with too much basic copolymers loses its function as a coating composition.

Properties and Uses of the Oral Composition

In some embodiments, the oral composition can form a film on a surface when contacted with an aqueous solution. In other embodiments, the oral composition of the present disclosure can form the film in less than about 30 seconds after the oral composition is contacted with water or dried with a stream of compressed air.

When the oral composition of the present disclosure contacts water, the water miscible solvents can diffuse into water and water can also diffuse into the oral composition. As a result, the molecular interaction among the copolymer chains can increase dramatically and then form a durable, toothbrush abrasion resistant and slippery film. Alternatively, the film can be formed by air drying. For example, air blowing can evaporate water and solvents to form the durable, brush abrasion resistant and slippery film.

The oral composition of the present disclosure can provide prolonged coating/film. In some embodiments, the film remains on at least 90% of the surface after brushing the surface for at least 5 strokes. In some other embodiments, the film remains on at least 90% of the surface after brushing the surface for at least 10 strokes. In other embodiments, the film remains on at least 90% of the surface after brushing the surface for at least 20 strokes. In yet other embodiments, the film remains on at least 90% of the surface after brushing the surface for at least 30 strokes. In some cases, the film remains on at least 90% of the surface after brushing the surface for at least 60 strokes. In other cases, the film remains on at least 90% of the surface after brushing the surface for at least 90 strokes. In yet other cases, the film remains on at least 90% of the surface after brushing the surface for at least 120 strokes.

In some embodiments, the film remains on at least 90% of the surface after brushing the surface for from 5 to 120 strokes. In some other embodiments, the film remains on at least 90% of the surface after brushing the surface for from 10 to 90 strokes. In other embodiments, the film remains on at least 90% of the surface after brushing the surface for from 20 to 60 strokes. In yet other embodiments, the film remains on at least 90% of the surface after brushing the surface for from 5 to 120 strokes.

Various methods can be employed to apply the oral composition on the dental structure. In some embodiments, the oral composition can be applied from the composition's container or dispenser such as a bottle, syringe, or tube. In some embodiments, a dental brush, microfiber, foam or sponge applicator or cotton Q tip is used to rub the surface of the dental structure and leave a thin layer of coating on the surface. In some other embodiments, a tray applicator, a dental tray, or a dental strip filled with the oral composition can be used. The oral composition can cover the surface of the dental structure and leave a layer of coating on the surface. In other embodiments, the oral composition can be sprayed (e.g. air-brushing) with a spray device or aerosol applicator onto the surface of the dental structure. In other embodiments, the oral composition can be directly painted onto the surface of the dental structure with a brush tip attached to a syringe. In yet other embodiments, the oral composition can be applied as a rinse. The oral composition can be set into a coating on the dental structure and its attachments within 30 seconds by water, saliva, or dried by air blowing.

Active Agents

In some embodiments, the oral composition of the present disclosure can include active agents. In other embodiments, the active agents can include, but are not limited to whitening agents, anticaries agents, fluoride-delivery agents, anti-gingivitis agents, tartar control agents, antiplaque agents, periodontal actives, breath freshening agents, malodor control agents, tooth desensitizers, salivary stimulants, flavors, biofilm disruptors, antimicrobials, anesthetic agent, pain killers, stain removal agents, coloring agents, remineralization agents, calculus-softening agents, and combinations thereof.

In various embodiments, the oral compositions of the present disclosure can include a whitening agent. As further discussed below, a "whitening agent" is a material which is effective to effect whitening of a tooth surface to which it is applied. In various embodiments, the oral compositions of the present disclosure can include a peroxide whitening agent, comprising a peroxide compound. As referred to herein, a "peroxide compound" is an oxidizing compound comprising a bivalent oxygen-oxygen group. Peroxide compounds can include, but are not limited to, peroxides and hydroperoxides, such as hydrogen peroxide, peroxides of alkali and alkaline earth metals, organic peroxy compounds, peroxy acids, pharmaceutically-acceptable salts thereof, and mixtures thereof. Peroxides of alkali and, alkaline earth metals can include, but are not limited to, lithium peroxide, potassium peroxide, sodium peroxide, magnesium peroxide, calcium peroxide, barium peroxide, and mixtures thereof. Organic peroxy compounds can include, but are not limited to, carbamide peroxide (also known as urea hydrogen peroxide), glyceryl hydrogen peroxide, alkyl hydrogen peroxides, dialkyl peroxides, alkyl peroxy acids, peroxy esters, diacyl peroxides, benzoyl peroxide, and monoperoxyphthalate, and mixtures thereof. Peroxy acids and their salts can include, but are not limited to, organic peroxy acids such as alkyl peroxy acids, and monoperoxyphthalate and mixtures thereof, as well as inorganic peroxy acid salts such as persulfate, dipersulfate, percarbonate, perphosphate, perborate and persilicate salts of alkali and alkaline earth metals such as lithium, potassium, sodium, magnesium, calcium and barium, and mixtures thereof. In various embodiments, the peroxide compound can include, but are not limited to, hydrogen peroxide, urea peroxide, sodium percarbonate and mixtures thereof. In one embodiment, the peroxide compounds can include hydrogen peroxide. In one embodiment, the peroxide compound can consist essentially of hydrogen peroxide.

The oral compositions of the present disclosure can include a non-peroxide whitening agent. Whitening agents among those useful herein can include non-peroxy compounds, such as chlorine dioxide, chlorites and hypochlorites. Chlorites and hypochlorites can include, but are not limited to, those of alkali and alkaline earth metals such as lithium, potassium, sodium, magnesium, calcium and barium. Non-peroxide whitening agents can also include, but are not limited to, colorants, such as titanium dioxide and hydroxyapatite.

The oral compositions of the present disclosure can include a tartar control (anticalculus) agent. Tartar control agents among those useful herein can include, but are not limited to, phosphates and polyphosphates (for example pyrophosphates), polyaminopropanesulfonic acid (AMPS), polyolefin sulfonates, polyolefin phosphates, diphosphonates such as azacycloalkane-2,2-diphosphonates (e.g., azacycloheptane-2,2-diphosphonic acid), N-methyl azacyclopentane-2,3-diphosphonic acid, ethane-1-hydroxy-1,1-diphosphonic acid (EHDP) and ethane-1-amino-1,1-diphosphonate, phosphonoalkane carboxylic acids and salts of any of these agents, for example their alkali metal and ammonium salts. Useful inorganic phosphate and polyphosphate salts can include, but are not limited to, monobasic, dibasic and tribasic sodium phosphates, sodium tripolyphosphate, tetrapolyphosphate, mono-, di-, tri- and tetrasodium pyrophosphates, sodium trimetaphosphate, sodium hexametaphosphate and mixtures thereof, wherein sodium can optionally be replaced by potassium or ammonium. Other useful anticalculus agents can include, but are not limited to, polycarboxylate polymers and polyvinyl methyl ether/maleic anhydride (PVME/MA) copolymers, such as those available under the Gantrez® from ISP, Wayne, N.J.

The oral compositions of the present disclosure can include a stannous ion source useful, for example, as a periodontal active, tartar control agent, anticaries agent or tooth desensitizer. Any orally acceptable stannous ion source can be used, including, but not limited to, stannous fluoride, other stannous halides such as stannous chloride dehydrate, organic stannous carboxylate salts such as stannous formate, acetate, gluconate, lactate, tartrate, oxalate, malonate and citrate, stannous ethylene glyoxide and the like.

The oral compositions of the present disclosure can include an antimicrobial (e.g., antibacterial) agent. Any orally acceptable antimicrobial agent can be used, including, but not limited to, Triclosan (5-chloro-2-(2,4-dichlorophenoxy)phenol); 8-hydroxyquinoline and salts thereof; zinc and stannous ion sources such as zinc citrate, zinc sulphate, zinc glycinate, sodium zinc citrate and stannous pyrophosphate; copper (II) compounds such as copper (II) chloride, fluoride, sulfate and hydroxide; phthalic acid and salts thereof such as magnesium monopotassium phthalate; sanguinarine; quaternary ammonium compounds, such as alkylpyridinium chlorides (e.g., cetylpyridinium chloride (CPC), combinations of CPC with zinc and/or enzymes, tetradecylpyridinium chloride, and N-tetradecyl-4-ethylpyridinium chloride); bisguanides, such as chlorhexidine digluconate, hexetidine, octenidine, alexidine; halogenated bisphenolic compounds, such as 2,2' methylenebis-(4-chloro-6-bromophenol); benzalkonium chloride; salicylanilide, domiphen bromide; iodine; sulfonamides; bisbiguanides; phenolics; piperidino derivatives such as delmopinol and octapinol; magnolia extract; grapeseed extract; thymol; eugenol; menthol; geraniol; carvacrol; citral; eucalyptol; catechol; 4-allylcatechol; hexyl resorcinol; methyl salicylate; antibiotics such as augmentin, amoxicillin, tetracycline, doxycycline, minocycline, metronidazole, neomycin, kanamycin and clindamycin; and mixtures thereof. A further illustrative list of useful antibacterial agents is described in detail in U.S. Pat. No. 5,776,435, which is incorporated herein by reference.

The oral compositions of the present disclosure can include an antioxidant. Any orally acceptable antioxidant can be used, including, but not limited to, butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, and mixtures thereof.

The oral compositions of the present disclosure can include a saliva stimulating agent, useful for example in amelioration of dry mouth. Any orally acceptable saliva stimulating agent can be used, including without limitation food acids such as citric, lactic, malic, succinic, ascorbic, adipic, fumaric, and tartaric acids, and mixtures thereof.

The oral compositions of the present disclosure can include a breath freshening agent. Any orally acceptable breath freshening agent can be used, including without limitation zinc salts such as zinc gluconate, zinc citrate and zinc chlorite, alpha-ionone and mixtures thereof.

The oral compositions of the present disclosure can include an antiplaque (e.g., plaque disrupting) agent. Any orally acceptable antiplaque agent can be used, including without limitation stannous, copper, magnesium and strontium salts, dimethicone copolyols such as cetyl dimethicone copolyol, papain, glucoamylase, glucose oxidase, urea, calcium lactate, calcium glycerophosphate, strontium polyacrylates and mixtures thereof.

In some embodiments, the antiplaque agent can include a compound of general Formula I or a pharmaceutically acceptable salt thereof:

$$HOCH_2\text{-}(CHOH)_n\text{-}CH_2NR^1R^2 \quad (I),$$

wherein $R^1$ and $R^2$ are independently selected from a hydrogen atom, an alkyl group, $C(O)R^3$, and $SO_2R^4$; $R^3$ and $R^4$ are independently selected from an alkyl group, an aryl group, and an aralkyl group; and n is an integer from 2 to 5. In some embodiments, the pharmaceutically acceptable salt is free of unsubstituted or substituted tropolone. In some embodiments, $R^1$ and $R^2$ each comprise a hydrogen atom, or are independently selected from a hydrogen atom and an alkyl group. In certain embodiments, $R^1$ or $R^2$ independently comprise an alkyl group of about one to about ten carbon atoms. In other embodiments, $R^1$ comprises a hydrogen atom and $R^2$ comprises $C(O)R^3$ or $SO_2R^4$. Typically, $R^3$ comprises an alkyl group having from about one to about twenty-six carbon atoms, more typically from about six to about sixteen carbon atoms. A further illustrative list of useful antiplaque agents is described in detail in U.S. Application & Publication No. US2013/0052146, which is incorporated herein by reference.

The oral compositions of the present disclosure can include an anti-inflammatory agent. Any orally acceptable anti-inflammatory agent can be used, including without limitation steroidal agents such as flucinolone and hydrocortisone, and nonsteroidal agents (NSAIDs) such as ketorolac, flurbiprofen, ibuprofen, naproxen, indomethacin, diclofenac, etodolac, indomethacin, sulindac, tolmetin, ketoprofen, fenoprofen, piroxicam, nabumetone, aspirin, diflunisal, meclofenamate, mefenamic acid, oxyphenbutazone, phenylbutazone, and mixtures thereof.

The oral compositions of the present disclosure can include an $H_2$ antagonist. $H_2$ antagonist useful herein include, but not limited to, cimetidine, etintidine, ranitidine, ICIA-5165, tiotidine, ORF-17578, lupititidine, donetidine, famotidine, roxatidine, pifatidine, lamtidine, BL-6548, BMY-25271, zaltidine, nizatidine, mifentidine, BMY-52368, SKF-94482, BL-6341A, ICI-162846, ramixotidine, Wy-45727, SR-58042, BMY-25405, loxtidine, DA-4634, bisfentidine, sufotidine, ebrotidine, HE-30-256, D-16637, FRG-8813, FRG-8701, impromidine, L-643728, HB-408.4, and mixtures thereof.

The oral compositions of the present disclosure can include a desensitizing agent. Desensitizing agents useful herein include, but not limited to, potassium citrate, potassium chloride, potassium tartrate, potassium bicarbonate, potassium oxalate, potassium nitrate, strontium salts, arginine and mixtures thereof. Alternatively or in addition a local or systemic analgesic such as aspirin, codeine, acetaminophen, sodium salicylate or triethanolamine salicylate can be used.

The oral compositions of the present disclosure can include a nutrient. Suitable nutrients can include without limitation, vitamins, minerals, amino acids, and mixtures thereof. Vitamins include, but not limited to, Vitamins C and D, thiamine, riboflavin, calcium pantothenate, niacin, folic acid, nicotinamide, pyridoxine, cyanocobalamin, para-aminobenzoic acid, bioflavonoids, and mixtures thereof. Nutritional supplements include, but not limited to, amino acids (such as L-tryptophane, L-lysine, methionine, threonine, levocarnitine and L-carnitine), lipotropics (such as choline, inositol, betaine, and linoleic acid), fish oil (including components thereof such as omega-3 (N-3) polyunsaturated fatty acids, eicosapentaenoic acid and docosahexaenoic acid), coenzyme Q10, and mixtures thereof.

The oral compositions of the present disclosure can include proteins. Suitable proteins can include, but are not limited to, milk proteins and enzymes such as peroxide-producing enzymes, amylase, and plaque-disrupting agents such as papain, glucoamylase, glucose oxidase.

The oral compositions of the present disclosure can include an inorganic or organic fluoride ion source useful, for example, as an anti-caries agent. Any orally acceptable fluoride ion source can be used, including without limitation potassium, sodium and ammonium fluorides and monofluorophosphates, stannous fluoride, indium fluoride and mixtures thereof. Organic fluorides sources can include tetralkylammonium fluoride or tetralkylammonium tetrafluorborate salts and the like. In various embodiments, water-soluble fluoride ion sources are used. In some other embodiments, the active agent can include at least two different fluoride salts. In other embodiments, the active agent can include, but is not limited to, sodium fluoride, strontium fluoride, calcium fluoride, zinc fluoride, calcium chloride, calcium nitrate, calcium phosphates, calcium hydrogen phosphate, calcium dihydrogen phosphate, and combinations thereof. In some embodiments, the active agent can provide a sustained fluoride release for at least 24 hours. As a result, the oral compositions of the present disclosure can, for example, provide a sustained fluoride release.

Methods of Delivering Aqueous Oral Compositions

In some embodiments, a method of delivering an oral composition of the present disclosure to a dental structure is provided. The method can include providing the oral composition; applying the oral composition to the dental structure; and contacting the oral composition with an aqueous solution, thereby forming a polymeric film on the dental structure.

Dental Structures with a Film Formed by Oral Compositions

As shown in FIG. 1, in some embodiments, a dental structure 10 is provided. The dental structure 10 can include a dental article 30, and a film 20 on a surface of the dental article. In these embodiments, the film can be formed by contacting an oral composition of the present disclosure with an aqueous solution or by drying the oral composition on the dental article. The oral composition can include an acidic copolymer, a neutral copolymer and optionally an active agent. The acidic copolymer can have acidic acrylate monomeric units, acidic methacrylate monomeric units, or a combination thereof. The neutral copolymer can have neutral acrylate monomeric units, neutral methacrylate monomeric units, or a combination thereof.

The following embodiments are intended to be illustrative of the present disclosure and not limiting.

Embodiments

Embodiment 1 is an oral composition, comprising:
  a solvent comprising water and a cosolvent chosen from lower alkyl alcohols, acetone and a combination thereof;
  an acidic copolymer comprising acidic acrylate monomeric units, acidic methacrylate monomeric units, or a combination thereof;
  a neutral copolymer comprising neutral acrylate monomeric units, neutral methacrylate monomeric units, or a combination thereof; and
  optionally an active agent;
  wherein the oral composition comprises from about 6 to about 18 wt-% of water, from about 30 to about 80 wt-% of cosolvent, from about 15 to about 50 wt-% of sum of the acidic and neutral copolymers, and the wt-% of each component is based on the total weight of the composition;
  wherein the acidic and neutral copolymers are dissolved in the oral composition; and
  wherein the oral composition is capable of forming a film on a surface when contacted with an aqueous solution.

Embodiment 2 is the oral composition of embodiment 1, wherein the cosolvent is ethanol.

Embodiment 3 is the oral composition of any preceding embodiment, wherein the oral composition comprises from about 8 to about 12 wt-% of water.

Embodiment 4 is the oral composition of any preceding embodiment, wherein the oral composition comprises from about 45 to about 60 wt-% of the cosolvent.

Embodiment 5 is an oral composition, comprising:
  a solvent chosen from lower alkyl alcohols, THF, DMSO, ionic liquid, TEC, ethyl acetate, acetone, and a combination thereof;
  an acidic copolymer comprising acidic acrylate monomeric units, acidic methacrylate monomeric units, or a combination thereof;
  a neutral copolymer comprising neutral acrylate monomeric units, neutral methacrylate monomeric units, or a combination thereof; and
  optionally an active agent;
  wherein the oral composition comprises from about 30 to about 80 wt-% of solvent, from about 15 to about 50 wt-% of sum of the acidic and neutral copolymers, and the wt-% of each component is based on the total weight of the composition;
  wherein the acidic and neutral copolymers are dissolved in the oral composition; and
  wherein the oral composition is capable of forming a film on a surface when contacted with an aqueous solution.

Embodiment 6 is the oral composition of embodiment 5, wherein the cosolvent is ethanol.

Embodiment 7 is the oral composition any preceding embodiment, wherein the oral composition is capable of forming the film in less than about 30 seconds after the oral composition is contacted with water.

Embodiment 8 is the oral composition of any preceding embodiment, wherein the consistency of the oral composition is from about 45 to about 110.

Embodiment 9 is the oral composition of any preceding embodiment, wherein the solvent further comprises at least one additional component chosen from isopropanol, propylene glycol, glycerin, low molecular weight polyethylene glycol, ethylene glycol based ester alcohols, and combinations thereof.

Embodiment 10 is the oral composition of any preceding embodiment, wherein the molecular weight of the acidic copolymer is from about 5,000 to about 500,000.

Embodiment 11 is the oral composition of any preceding embodiment, wherein the molecular weight of the neutral copolymer is from about 10,000 to about 100,000.

Embodiment 12 is the oral composition of any preceding embodiment, wherein the oral composition comprises from about 20 to about 48 wt-% of the sum of the acidic and neutral copolymers.

Embodiment 13 is the oral composition of any preceding embodiment, wherein the oral composition comprises from about 22 to about 37 wt-% of the sum of the acidic and neutral copolymers.

Embodiment 14 is the oral composition of any preceding embodiment, wherein the acidic copolymer is chosen from Eudragit 5100, Eudragit L100, Eudragit L100-55, AC210 and combinations thereof.

Embodiment 15 is the oral composition of any preceding embodiment, wherein the neutral copolymer is chosen from Eudragit RS100 and Eudragit RL 100.

Embodiment 16 is the oral composition of any preceding embodiment, wherein the film remains on at least 90% of the surface after brushing the surface for at least 5 strokes.

Embodiment 17 is the oral composition of any preceding embodiment, wherein the film remains on at least 90% of the surface after brushing the surface for at least 10 strokes.

Embodiment 18 is the oral composition of any preceding embodiment, wherein the film remains on at least 90% of the surface after brushing the surface for at least 20 strokes.

Embodiment 19 is the oral composition of any preceding embodiment, wherein the film remains on at least 90% of the surface after brushing the surface for at least 30 strokes.

Embodiment 20 is the oral composition of any preceding embodiment, wherein the film remains on at least 90% of the surface after brushing the surface for at least 60 strokes.

Embodiment 21 is the oral composition of any preceding embodiment, wherein the film remains on at least 90% of the surface after brushing the surface for at least 90 strokes.

Embodiment 22 is the oral composition of any preceding embodiment, wherein the film remains on at least 90% of the surface after brushing the surface for at least 120 strokes.

Embodiment 23 is the oral composition of any preceding embodiment, wherein the film remains on at least 90% of the surface after brushing the surface for from 5 to 120 strokes.

Embodiment 24 is the oral composition of any preceding embodiment, wherein the film remains on at least 90% of the surface after brushing the surface for from 10 to 90 strokes.

Embodiment 25 is the oral composition of any preceding embodiment, wherein the film remains on at least 90% of the surface after brushing the surface for from 20 to 60 strokes.

Embodiment 26 is the oral composition of any preceding embodiment, wherein the film remains on at least 90% of the surface after brushing the surface for from 5 to 120 strokes.

Embodiment 27 is the oral composition of any preceding embodiment, wherein the oral composition further comprises a basic copolymer comprising basic acrylate monomeric units, basic methacrylate monomeric units, or a combination thereof.

Embodiment 28 is the oral composition of embodiment 27, wherein the oral composition comprises from about 0 to about 1.0 wt-% of the basic copolymer.

Embodiment 29 is the oral composition of embodiments 27-28, wherein the oral composition comprises from about 0.1 to about 0.4 wt-% of the basic copolymer.

Embodiment 30 is the oral composition of embodiments 27-29, wherein the weight ratio of the basic copolymer to the acidic polymer is from about 0 to about 1:10.

Embodiment 31 is the oral composition of embodiments 27-30, wherein the weight ratio of the basic copolymer to the acidic polymer is from about 1:100 to about 1:15.

Embodiment 32 is the oral composition of embodiments 27-31, wherein the basic copolymer is chosen from Eudragit E100 and other copolymer containing dimethylaminoethyl methacrylate for ionic crosslinking.

Embodiment 33 is the oral composition of embodiments 27-32, wherein the molecular weight of the basic copolymer is from about 10,000 to about 100,000.

Embodiment 34 is the oral composition of any preceding embodiment, wherein the active agent is selected from whitening agents, anticaries agents, fluoride-delivery agents, anti-gingivitis agents, tartar control agents, anti-plaque agents, periodontal actives, breath freshening agents, malodor control agents, tooth desensitizers, salivary stimulants, flavors, biofilm disruptors, antimicrobials, anesthetic agent, pain killers, stain removal agents, coloring agents, remineralization agents, calculus-softening agents, and combinations thereof.

Embodiment 35 is the oral composition of any preceding embodiment, wherein the active agent is a fluoride composition.

Embodiment 36 is the oral composition of any preceding embodiment, wherein the active agent provides a sustained fluoride release for at least 24 hours.

Embodiment 37 is the oral composition of any preceding embodiment, wherein the active agent comprises at least two different fluoride salts.

Embodiment 38 is the oral composition of any preceding embodiment, wherein the active agent is chosen from sodium fluoride, strontium fluoride, calcium fluoride, zinc fluoride, calcium chloride, calcium nitrate, calcium phosphates, calcium hydrogen phosphate, calcium dihydrogen phosphate, and combinations thereof.

Embodiment 39 is an oral composition, comprising:
a solvent comprising water and a cosolvent chosen from lower alkyl alcohols, acetone and a combination thereof;
an acidic copolymer chosen from Eudragit 5100, Eudragit L100, Eudragit L100-55, AC210 and combinations thereof;
a neutral copolymer chosen from Eudragit RS100 and Eudragit RL 100; Eudragit E100; and
optionally a fluoride salt;
wherein the oral composition comprises from about 8 to about 12 wt-% of water, from about 30 to about 80 wt-% of cosolvent, from about 15 to about 50 wt-% of sum of the acidic and neutral copolymers;
wherein the acidic and neutral copolymers are dissolved in the oral composition; and
wherein the oral composition is capable of forming a film on a surface when contacted with an aqueous solution.

Embodiment 40 is a method of delivering an oral composition to a dental structure comprising:
providing an oral composition;
applying the oral composition to the dental structure; and
contacting the oral composition with an aqueous solution, thereby forming a polymeric film on the dental structure.

Embodiment 41 is the method of embodiment 40, wherein the oral composition comprises
a solvent comprising water and a cosolvent chosen from lower alkyl alcohols and acetone;
an acidic copolymer comprising acidic acrylate monomeric units, acidic methacrylate monomeric units, or a combination thereof;
a neutral copolymer comprising neutral acrylate monomeric units, neutral methacrylate monomeric units, or a combination thereof; and
optionally an active agent;
wherein the acidic and neutral copolymers are dissolved in the oral composition.

Embodiment 42 is the method of embodiment 40, wherein the oral composition comprises a solvent chosen from lower alkyl alcohols, THF, DMSO, ionic liquid, TEC, ethyl acetate, acetone, and a combination thereof;

an acidic copolymer comprising acidic acrylate monomeric units, acidic methacrylate monomeric units, or a combination thereof;

a neutral copolymer comprising neutral acrylate monomeric units, neutral methacrylate monomeric units, or a combination thereof; and optionally an active agent;

wherein the acidic and neutral copolymers are dissolved in the oral composition.

Embodiment 43 is a dental structure, comprising:

a dental article, and a film on a surface of the dental article, wherein the film is formed by contacting an oral composition with an aqueous solution or by drying the oral composition on the dental article;

wherein the oral composition comprises:

an acidic copolymer comprising acidic acrylate monomeric units, acidic methacrylate monomeric units, or a combination thereof;

a neutral copolymer comprising neutral acrylate monomeric units, neutral methacrylate monomeric units, or a combination thereof; and optionally an active agent.

Embodiment 44 is the dental structure of embodiment 43, wherein the oral composition further comprises a solvent comprising water and a cosolvent chosen from lower alkyl alcohols and acetone, wherein the oral composition comprises from about 6 to about 18 wt-% of water, from about 30 to about 80 wt-% of cosolvent, from about 15 to about 50 wt-% of sum of the acidic and neutral copolymers, and the wt-% of each component is based on the total weight of the composition; and wherein the acidic and neutral copolymers are dissolved in the oral composition.

Embodiment 45 is the dental structure of embodiment 43, wherein the oral composition further comprises a solvent chosen from lower alkyl alcohols, THF, DMSO, ionic liquid, TEC, ethyl acetate, acetone, and a combination thereof;

wherein the oral composition comprises from about 30 to about 80 wt-% of solvent, from about 15 to about 50 wt-% of sum of the acidic and neutral copolymers, and the wt-% of each component is based on the total weight of the composition; and wherein the acidic and neutral copolymers are dissolved in the oral composition The following working examples are intended to be illustrative of the present disclosure and not limiting.

EXAMPLES

Objects and advantages of this invention are further illustrated by the following examples, but the particular materials and amounts thereof recited in these examples, as well as other conditions and details, should not be construed to unduly limit this invention.

The materials used to prepare examples of the invention (Ex) as well as comparative examples (CE) are outlined below.

Materials

| Material | Description | Source |
| --- | --- | --- |
| AEROSIL R812S | Hydrophobic fumed silica | Evonic Degussa Corp, Pasippany, NJ |
| EUDRAGIT RS100 | Neutral copolymer of ethyl acrylate, methyl methacrylate and a low content of methacrylic acid ester with quaternary ammonium groups | Evonic Industries, Darmstadt, Germany |
| EUDRAGIT RL100 | Neutral copolymer of ethyl acrylate, methyl methacrylate and a low content of methacrylic acid ester with quaternary ammonium groups | Evonic Industries, Darmstadt, Germany |
| EUDRAGIT S100 | Acidic anionic copolymer based on methacrylic acic and methyl methacrylate | Evonic Industries, Darmstadt, Germany |
| EUDRAGIT L100-55 | Acidic anionic copolymer based on methacrylic acid and ethyl acrylate | Evonic Industries, Darmstadt, Germany |
| EUDRAGIT E100 | Basic cationic copolymer based on dimethylaminoethyl methacrylate, butyl methacrylate, and methyl methacrylate | Evonic Industries, Darmstadt, Germany |
| AC210 | Acidic liquid acrylate polymer | Lubrizol, Wicliffe, OH |
| DEGEE | Diethylene glycol monoethyl ether 98% | Alfa Aesar, Ward Hill, MA |
| GANTREZ ES225 | Monoalkyl ester of poly(methyl vinyl ether/maleic acid) 50/50 in ethanol | ISP Chemicals, Calvert City, KY |
| PLURONIC F127NF | Block copolymer of ethylene oxide and propylene oxide | BASF, Florham Park, NJ |
| GANTREZ ES425 | Butyl Ester of Polyvinylmethylether/Maleic Anhydride Copolymer 50/50 in ethanol | ISP Chemicals, Calvert City, KY |
| PEG 300 | Polyethylene glycol 300 | Univar (Distributer for Dow), Los Angeles, CA |

| Material | Description | Source |
|---|---|---|
| CARBOPOL 971P NF | Crosslinked polyacrylic acid | Lubrizol |
| Xylitol | Flavor and sweetener | Sigma-Aldrich, St Louis, MO |
| PEI | Polyethyleneimine | BASF, Florham Park, NJ |
| Chitosan | Basic polymer | Sigma-Aldrich, St Louis, MO |
| Mint | Mint flavor | Foote & Jenks Corp, Camden, NJ |
| EtOH | Ethanol, 200 proof, USP grade | Columbus Chemical Industries, Columbus, WI |
| PPG | Propylene glycol, USP grade | EMD Billerica, MA |
| Glycerol | USP grade | Sigma-Aldrich, St Louis, MO |
| Acetone | | Alfa Aesar, Ward Hill, MA |
| EtOAc | Ethyl acetate | Alfa Aesar, Ward Hill, MA |
| $CaF_2$ | Calcium fluoride | Alfa Aesar, Ward Hill, MA |
| $NH_4F$ | Ammonium fluoride | Sigma-Aldrich, St Louis, MO |
| NaF | milled sodium fluoride (passed through 30micro screen) | 3M ESPE, St Paul, MN |
| $K_3PO_4$ | Potassium Phosphate Tribasic | JT Baker Phillipsburg, NJ |
| NaCl | Sodium chloride | EMD Billerica, MA |
| $Ca_2Cl_2 \cdot 2H_2O$ | Calcium chloride | EMD Billerica, MA |
| KCl | Potassium chloride | EMD Billerica, MA |
| Gastric Mucin | Sigma porcine stomach mucin type II | Sigma Aldrich |
| $KH_2PO_4$ | Potassium dihydrogen phosphate | JT Baker Phillipsburg, NJ |
| NaOH | Sodium hydroxide | Alfa Aesar |
| IPA | Iso propanol | Alfa Aesar, Ward Hill, MA |
| Micro $TiO_2$ | Titanium dioxide colorant | Evonic Degussa Corp, Pasippany, NJ |
| Precolor $TiO_2$ | Titanium dioxide colorant | Universal Preserv-a-chem, Somerset, NJ |
| Ultramarine Blues | Nubiperf AR Ultramarine Blues | NUBIOLA USA, Norcross, GA |
| Invisible blue | DayGlo A-594-5 | Dayglo color Corp. Cleveland OH |
| 1-propanol | | Alfa Aesar, Ward Hill, MA |
| Ionic liquid | Tris(2-hydroxyethyl) methylammonium methylsulfate | Sigma-Aldrich, St Louis, MO |
| DMSO | Dimethyl sulfoxide | Sigma-Aldrich, St Louis, MO |
| THF | tetrahydrofuran | Alfa Aesar, Ward Hill, MA |
| TEC | Triethyl citrate | Alfa Aesar, Ward Hill, MA |

Preparation of Oral (Coating) Compositions

Polymer solutions were prepared by first weighing the designated amount of solvent into either a 250 ml or 30 ml glass jar that has a cap. The designated amount of polymer material was then added to the jar. The jar was sealed and then placed on a Wheaton Culture Roller for 2-3 days (~30 rpm) until the polymer was completely dissolved in the solvent. Additional ingredients such as NaF, other salts, viscosity modifiers, flavorings, etc. were added to the polymer solution using two 2 minute cycles in a speed mixer (SpeedMixer DAC150.1 FVZ available from FlacTek, Inc., Landrum, S.C.) set at 3000 rpm. The materials used in each coating composition as well as the amount (in grams) are shown in the examples and tables below.

Preparation of Artificial Saliva

Artificial saliva was prepared with following procedure: 3.52 g of gastric mucin, 0.610 g NaCl, 0.341 g $CaCl_2.2H_2O$, 1.183 g $KH_2PO_4$ and 1.179 g KCL were weighed into a 2000 ml flask. 1600 ml of deionized (DI) water was slowly added using a magnetic stir bar to mix solution until all solids are dissolved. The pH was adjusted to 7.0 with 50% NaOH solution.

Test Methods

Coating Evaluation—Feel, Set, Adhesion and Abrasion Resistance Test

Compositions of the present disclosure and comparative compositions were coated onto a glass (or plastic if noted) slide (available from VWR, Radnor Pa.) or bovine teeth using a cotton swab or small brush. The coated substrate was then dipped into a container of tap water for 30 seconds at room temperature (~25° C.). The coating was then qualitatively evaluated to determine if a film had formed ("set") and what the feel of that film was ("hard", "soft" or "sticky"). Additionally the set films were evaluated for their adhesion to the substrate. Adhesion was deemed "good" when the set film could not be pushed away by finger pressure and "no" when the set film could be pushed away by finger pressure. Abrasion resistance was evaluated by brushing the set coating with a tooth brush and counting the number of brush strokes required to remove the coating.

Fluoride Release Test

Approximately 40-50 mg of coating composition was evenly painted onto a 1 inch×1 inch (2.54 cm×2.54 cm) plastic slide (RINZYL plastic micro slide available from VRW, Radnor, Pa.). The coated slide was immersed in 25 ml of deionized water in a plastic test tube for 1 hour. After 1 hour, the slide was removed, rinsed and then immersed in a second 25 ml aliquot of water in another test tube. After 3 more hours (4 hours total), the process was repeated and the slide was immersed in a third 25 ml aliquot of water. After 2 more hours (6 hours total) the process was again repeated and the slide was placed in a fourth 25 ml aliquot of water where it remained for an additional 18 hours (24 hours total) before being removed. Each of the 25 ml aliquots of deionized water were then evaluated for fluoride concentration. 10 ml of the sample solutions from above preparation were mixed with 10 ml of TISAB II to make the solution for fluoride concentration measurements. The fluoride concentrations were measured using a Cole Parmer fluoride ion meter equipped with a fluoride combination electrode which had been standardized using standard concentrations of fluoride buffered with TISAB II. Five replicate samples were run to get an average. The fluoride concentration was measured in parts per million and the fluoride release was reported as $\mu gF/cm^2$ coating using the following equation.

$$\mu F/cm^2 \text{ coating} = \frac{(\text{Concentration of } F \text{ in ppm}) * (\text{sample volume in mL})}{(\text{coating area in } cm^2)}$$

Fluoride Uptake on Bovine Enamel Test

Bovine teeth were potted in a poly(methyl)methacrylate resin and then polished with 320 grit sandpaper to expose the enamel surface. Half of the exposed surface was then coated with about 15 mg of polymer composition. The other half of the exposed enamel was coated with nail polish as a mask. The coated teeth were then placed in 50 ml of artificial saliva at 37° C. for either 30 minutes or 24 hours. After the allotted time, the teeth were removed from the artificial saliva and rinsed with water. The coated teeth were then rinsed with an ethanol/acetone solution to remove the coating and then finally rinsed with water to get a clean surface. A Hitachi TM3000 table top scanning electron microscope was used to determine the fluoride atom % on the surface of the teeth. Three data points were collected and averaged for each coating.

Liquid Consistency

The liquid consistency is a measurement of the viscosity of the coating compositions. Consistency was determined by placing 0.15 g of coating liquid in the center of a 4×4 inch (10.2×10.2 cm) a first glass plate. A second identical glass plate was then placed on top of the first glass plate, sandwiching the coating liquid between the two plates. A 2 pound (0.91 kg) compression weight was placed on top of the second plate for 2 minutes. The weight was then removed and three diameter measurements of the compressed liquid were made at 120° intervals around the circle formed by the compressed by the compressed sample. Measurements were made to the nearest 1/32 inch (0.79 mm). All measurements were made through the top plate taking care not to put any pressure on the plate while making the measurements. The average of the three measurements was reported (in 1/32 of an inch). Consistency measurements of 45-110 (35-87 mm) were deemed acceptable.

Abrasion Resistance Tooth Brush Testing

Bovine teeth were potted in a poly(methyl)methacrylate (PMMA) resin and then polished with 320 grit sandpaper to expose the enamel surface. The exposed enamels were wiped with paper tower to remove excess of water, then coated with about 10 mg materials to form a thin layer on enamel, and then stored in 37° C. artificial saliva for varying amounts of time. A tooth brush machine (available from Foth Production Solution, LLC, Greenbay Wis.) was used to test coating wear durability on enamel. Tooth brush head was cut from tooth brush with brand name Acclean gental care from Henry Schein and inserted into the fixture on the tooth brush machine. The potted bovine teeth were inserted and fixed in a plastic port filled with brush media. The tooth brush head was rest on the coating surface. The machine can control the tooth brush head moving back and forth against the coating on enamel. The brushing stroke is defined as brushing the surface back and forth one time. 5 ml of 1:1 water and tooth paste (CREST cavity protection tooth paste) mixture was used as brush media. After certain brushing strokes, the coating surfaces were checked and the amount of wear was estimated.

Sample Preparation for SEM of Dentin Surface

Bovine teeth were potted in PMMA resin and then polished with 320 grit sandpaper to expose dentin. SCOTCHBOND etchant (available from 3M Company, St. Paul, Minn.) was used to etch the tooth surface for 10 seconds and then rinsed with water to remove the smear layer and expose the dentin tubules. Half of the exposed dentin was then coated about 15 mg of coating solution and the other half of the exposed dentin was left uncoated. The tooth was then put into 20 ml of artificial saliva at 37° C. for 30 minutes, and then rinsed with water. Scanning electron micrograph (SEM) images of the dentin surface were taken using a Hitachi TM3000 table top microscope Comparative Examples 1-10

Various Polymer Coating Compositions

Coating compositions were prepared and coated as described above using the materials and amounts (in grams) as outlined in Table 1 below. Coated films were evaluated for set, feel and adhesion as described above.

TABLE 1

|  | CE 1 | CE 2 | CE 3 | CE 4 | CE 5 | CE 6 | CE 7 | CE 8 | CE 9 | CE 10 |
| --- | --- | --- | --- | --- | --- | --- | --- | --- | --- | --- |
| EUDRAGIT L100-55 | 0 | 0 | 0 | 0 | 0 | 2 | 4 | 4 | 0 | 0 |
| AC210 | 20 | 0 | 0 | 5.44 | 10 | 10 | 0 | 0 | 0 | 0 |
| PEG300 | 0 | 2 | 2 | 0 | 0 | 0 | 0 | 0 | 0 | 0 |
| GANTREZ ES425 | 0 | 8 | 8 | 0 | 5 | 0 | 0 | 0 | 0 | 0 |
| EtOH | 3.75 | 0 | 0 | 5 | 5 | 5 | 6 | 6 | 1 | 3 |
| GANTREZ ES225 | 0 | 0 | 0 | 5 | 0 | 0 | 0 | 0 | 10 | 10 |
| $K_3PO_4$ | 0 | 0 | 0 | 0 | 0 | 0 | 0.5 | 0.5 | 0.2 | 0.2 |
| DI Water | 1.25 | 1 | 0 | 0 | 1 | 1 | 4 | 2 | 4 | 2 |
| Film feel | sticky | hard | hard | soft | soft | soft | hard | hard | hard | hard |
| Set in water | yes | yes | yes | yes | yes | yes | yes | yes | yes | yes |
| Film adhesion | no | no | no | no | no | no | no | no | no | no |

Examples 1-3 & Comparative Examples 11-15

Compositions with Water and Ethanol

Coating compositions were prepared and coated as described above using the materials and amounts (in grams) as outlined in Table 2 below. Coated films were evaluated for set, feel and adhesion as described above.

TABLE 2

|  | CE 11 | CE 12 | Ex 1 | Ex 2 | CE 13 | CE 14 | CE 15 | Ex 3 |
|---|---|---|---|---|---|---|---|---|
| EUDRAGIT RS100 | 10 | 20 | 15 | 10 | 20 | 20 | 20 | 10 |
| EtOH | 40 | 59.85 | 59.85 | 59.85 | 59 | 59.85 | 59 | 50 |
| DI Water | 0 | 15 | 15 | 15 | 15 | 15 | 15 | 10 |
| EUDRAGIT S100 | 0 | 5 | 10 | 15 | 5 | 0.15 | 1 | 15 |
| EUDRAGIT E100 | 0 | 0.15 | 0.15 | 0 | 1.0 | 5 | 20 | 0 |
| Polymer solubility: formed solution | no | no | yes | yes | no | no | no | yes |
| Film feel | — | — | hard | hard | — | — | — | hard |
| Set in water | — | — | yes | yes | — | — | — | yes |
| Film adhesion | — | — | good | good | — | — | — | good |

Example 4 & Comparative Examples 16-18

Compositions with Basic Polymers

Coating compositions were prepared and coated as described above using the materials and amounts (in grams) as outlined in Table 3 below.

TABLE 3

|  | Ex 4 | CE 16 | CE 17 | CE 18 |
|---|---|---|---|---|
| EUDRAGIT S100 | 15 | 15 | 15 | 15 |
| EtOH | 59.85 | 60 | 60 | 60 |
| PEI | 0 | 0.2 | 0 | 0 |
| Chitosan | 0 | 0 | 0.2 | 0 |
| DI Water | 15 | 14.8 | 14.8 | 14 |
| EUDRAGIT RS100 | 10 | 10 | 10 | 10 |
| EUDRAGIT E100 | 0.15 | 0 | 0 | 1.0 |
| Polymer solubility: formed solution | yes | No formed gel | No formed gel | No formed gel |

Examples 5-11 & Comparative Examples 19-20

Compositions with Water/Ethanol/PPG Solvent

Coating compositions were prepared and coated as described above using the materials and amounts (in grams) as outlined in Table 4 below. Coated films were evaluated for set, feel and adhesion as described above.

TABLE 4

|  | Ex 5 | Ex 6 | CE 19 | Ex 7 | Ex 8 | Ex 9 | Ex 10 | Ex 11 | CE 20 |
|---|---|---|---|---|---|---|---|---|---|
| EUDRAGIT S100 | 7.5 | 24 | 7.5 | 18 | 15 | 15 | 15 | 7.5 | 7.5 |
| EtOH | 25 | 110 | 15.95 | 117 | 52 | 52 | 53.85 | 21.25 | 17.5 |
| PPG | 6.5 | 24 | 13.47 | 25.5 | 11.85 | 12 | 10 | 5.35 | 10 |
| DI Water | 6 | 26 | 8 | 27.5 | 11 | 11 | 11 | 10.825 | 9.925 |
| EUDRAGIT RS100 | 4.75 | 16 | 4.5 | 12 | 10 | 10 | 10 | 5 | 5 |
| EUDRAGIT E100 | 0.25 | 0.24 | 0.5 | 0.18 | 0.15 | 0 | 0.015 | 0.075 | 0.075 |
| Polymer solubility: formed solution | yes | yes | no | yes | yes | yes | yes | yes | no |
| Film feel | hard | hard | — | hard | hard | hard | hard | hard | — |
| Set in water | yes | yes | — | yes | yes | yes | yes | yes | — |
| Film adhesion | good | good | — | good | good | good | good | good | — |

Examples 12-19 & Comparative Examples 21-23

Compositions with Water/Ethanol/Glycerol Solvent

Coating compositions were prepared and coated as described above using the materials and amounts (in grams) as outlined in Table 5 below. Coated films were evaluated for set, feel and adhesion as described above.

TABLE 5

|  | Ex 12 | Ex 13 | CE 21 | Ex 14 | CE 22 | Ex 15 | CE 23 | Ex 16 | Ex 17 | Ex 18 | Ex 19 |
|---|---|---|---|---|---|---|---|---|---|---|---|
| EUDRAGIT S100 | 7.5 | 7.5 | 7.5 | 28 | 7.5 | 7.5 | 7.5 | 7.5 | 12 | 11.96 | 8.83 |
| Ethanol | 21.25 | 21.25 | 15.95 | 104 | 17.5 | 25 | 17.5 | 26.5 | 51.7 | 52.81 | 51.25 |
| DI water | 8 | 5.15 | 8 | 26 | 10 | 10 | 6 | 8 | 12.5 | 12.72 | 15.53 |
| glycerol | 8.175 | 11.025 | 13.475 | 30 | 9.925 | 2.425 | 13.925 | 2.925 | 12.5 | 12.72 | 12.42 |
| EUDRAGIT E100 | 0.075 | 0.075 | 0.075 | 0.3 | 0.075 | 0.075 | 0.075 | 0.075 | 0.3 | 0.225 | 0.2 |
| EUDRAGIT RS100 | 5 | 5 | 5 | 20 | 5 | 5 | 5 | 5 | 11 | 9.56 | 11.77 |
| Polymer solubility: formed solution | yes | yes | no | yes | no | yes | no | yes | yes | yes | yes |
| Film feel | hard | hard | — | hard | — | hard | — | hard | hard | hard | hard |
| Set in water | yes | yes | — | yes | — | yes | — | yes | yes | yes | yes |
| Film adhesion | good | good | — | good | — | good | — | good | good | good | good |

Examples 20-22 & Comparative Examples 24-25

Compositions with Water/Ethanol/Glycerol/DEGEE as Solvents

Coating compositions were prepared and coated as described above using the materials and amounts (in grams) as outlined in Table 6 below. Coated films were evaluated for set, feel and adhesion as described above.

TABLE 6

|  | Ex 20 | Ex 21 | CE 24 | CE 25 | Ex 22 |
|---|---|---|---|---|---|
| EUDRAGIT S100 | 15 | 15 | 6 | 6 | 28 |
| Ethanol | 30 | 0 | 0 | 0 | 0 |
| DEGEE | 35 | 55 | 27.5 | 27.5 | 96 |
| DI water | 10 | 8 | 0 | 0 | 16 |
| glycerol | 0 | 0 | 0 | 6.5 | 0 |
| PPG | 0 | 10 | 6.5 | 0 | 40 |
| EUDRAGIT E100 | 0 | 0 | 0 | 0 | 0.4 |
| EUDRAGIT RS100 | 10 | 12 | 6 | 6 | 20 |
| Polymer solubility: formed solution | yes | yes | no | no | yes |
| Film feel | hard | hard | — | — | hard |
| Set in water/saliva | yes | yes | — | — | yes |
| Film adhesion | good | good | — | — | good |

Examples 23-26

Compositions with Water/Ethanol/PPG as Solvents

Coating compositions were prepared and coated as described above using the materials and amounts (in grams) as outlined in Table 7 below. Coated films were evaluated for set, feel, adhesion and abrasion resistance as described above.

TABLE 7

|  | Ex 23 | Ex 24 | Ex 25 | Ex 26 |
|---|---|---|---|---|
| EUDRAGIT S100 | 0 | 15 | 0 | 15 |
| EtOH | 52 | 52 | 53.85 | 52 |
| PPG | 11.85 | 11.85 | 10 | 12 |
| DI Water | 11 | 11 | 11 | 11 |
| EUDRAGIT RS100 | 10 | 10 | 0 | 10 |
| EUDRAGIT E100 | 0.15 | 0.15 | 0.15 | 0 |
| EUDRAGIT RL100 | 0 | 0 | 10 | 0 |
| EUDRAGIT L100 | 15 | 0 | 15 | 0 |
| Film feel | hard | hard | soft | hard |
| Set in water | yes | yes | yes | yes |
| Film adhesion | good | good | good | good |
| Brush wear out strokes | 30 | 50 | 10 | 20 |

Examples 27-28 & Comparative Example 26

Abrasion Resistance and Fluoride Uptake on Bovine Tooth Enamel

Coating compositions were prepared as described above using the materials and amounts (in grams) as outlined in Table 8 below. The coating compositions were applied to bovine teeth as described above, and then immersed in artificial saliva for either 30 minutes or 24 hours. The abrasion resistance was determined as described above by counting the number of brush strokes required to remove the set film. The fluoride uptake on the bovine tooth enamel was then measured as described above.

TABLE 8

|  | Ex 27 | Ex 28 |
|---|---|---|
| EUDRAGIT S100 | 28 | 30 |
| EtOH | 0 | 104 |
| PPG | 40 | 0 |
| DI Water | 16 | 26 |
| EUDRAGIT RS100 | 20 | 20 |
| DEGEE | 96 | 0 |
| EUDRAGIT E100 | 0.4 | 0.3 |
| Glycerol | 0 | 20 |
| NaF | 5.3 | 5.2 |
| $CaF_2$ | 0 | 2.0 |
| Strokes for 0.5 hr in artificial saliva | 15 | 100 |
| Strokes for 24 hr in artificial saliva | 15 | 100 |
| F on tooth for 0.5 hr in artificial saliva | 4.61% | 5.43% |
| F on tooth for 24 hr in artificial saliva | 5.25% | 10.4% |

Examples 29-33

Compositions with Additives

Coating compositions were prepared and coated as described above using the materials and amounts (in grams) as outlined in Table 9 below. Coated films were evaluated for set, feel and adhesion as described above.

TABLE 9

|  | Ex 29 | Ex 30 | Ex 31 | Ex 32 | Ex 33 |
|---|---|---|---|---|---|
| EUDRAGIT S100 | 15 | 15 | 26 | 30 | 26 |
| Ethanol | 52 | 52 | 100 | 104 | 108 |
| DI water | 11 | 11 | 29 | 22 | 26 |
| glycerol | 11.85 | 11.85 | 0 | 0 | 20 |
| PPG | 0 | 0 | 28 | 23.8 | 0 |
| EUDRAGIT E100 | 0.15 | 0.15 | 0.25 | 0.2 | 0.3 |
| EUDRAGIT RS100 | 10 | 10 | 17 | 20 | 20 |
| Xylitol | 1.6 | 5 | 6.6 | 0 | 0 |
| AEROSIL R812S | 0 | 0 | 6.6 | 0 | 0 |
| NaF | 0 | 0 | 6.8 | 0 | 0 |
| Mint | 0 | 0 | 1.2 | 0 | 0 |
| CARBOPOL 917P NF | 0 | 0 | 0 | 2.6 | 0 |
| PLURONIC F127NF | 0 | 0 | 0 | 0 | 2.0 |
| Film feel | hard | hard | hard | hard | hard |
| Set in water | yes | yes | yes | yes | yes |
| Film adhesion | good | good | good | good | good |

Examples 34-52

Fluoride Release

Coating compositions containing fluoride were prepared and coated as described above using the materials and amounts (in grams) as outlined in Table 10 below. Films formed on 1 inch×1 inch (2.54 cm×2.54 cm) plastic slides were then evaluated for fluoride release as described above.

TABLE 10

|  | Ex. 34 | Ex. 35 | Ex. 36 |
|---|---|---|---|
| Eudragit S100 | 30 | 30 | 24 |
| EtOH | 104 | 104 | 110 |
| DI Water | 26 | 26 | 26 |
| Eudragit RS100 | 20 | 20 | 20 |
| Eudragit E100 | 0.3 | 0.3 | 0.3 |
| glycerin | 20 | 20 | 20 |
| Potassium zinc fluoride | 0 | 0 | 1.5 |
| Encapsulated NaF | 0 | 3.0 | 0 |
| NaF | 2.6 | 0 | 2.25 |
| Cumulative Fluoride Release 1 hr | 69.8 | 92.85 | 87.3 |
| Cumulative Fluoride Release 4 hr | 70.5 | 93.4 | 88.3 |
| Cumulative Fluoride Release 6 hr | 70.6 | 93.5 | 88.6 |
| Cumulative Fluoride Release 24 hr | 70.8 | 93.8 | 88.8 |

Coating compositions containing various combinations of fluoride salts were prepared and coated as described above using the materials and amounts (in grams) as outlined in Table 11 below. These coatings show sustained fluoride release. Films formed on 1 inch×1 inch (2.54 cm×2.54 cm) plastic slides were then evaluated for fluoride release as described above.

TABLE 11

|  | Ex. 37 | Ex. 38 | Ex. 39 | Ex. 40 |
|---|---|---|---|---|
| Eudragit S100 | 26 | 26 | 26 | 26 |
| EtOH | 108 | 108 | 108 | 108 |
| DI Water | 26 | 26 | 26 | 26 |
| Eudragit RS100 | 20 | 20 | 20 | 20 |
| Eudragit E100 | 0.3 | 0.3 | 0.3 | 0.3 |
| glycerin | 20 | 20 | 20 | 20 |
| CaF$_2$ | 0.5 | 0.9 | 0 | 0 |
| SrF$_2$ | 0.5 | 0 | 1.5 | 0 |
| MgF$_2$ | 0.5 | 0 | 0 | 0.725 |
| NaF | 3.25 | 2.25 | 2.25 | 2.25 |
| Cumulative Fluoride Release 1 hr | 82.31 | 80.91 | 83.93 | 88.04 |
| Cumulative Fluoride Release 4 hr | 89 | 83.7 | 98.5 | 89.6 |
| Cumulative Fluoride Release 6 hr | 90.8 | 85.2 | 103.6 | 90.3 |
| Cumulative Fluoride Release 24 hr | 103.6 | 94.4 | 115.2 | 102.7 |

Coating compositions containing various combinations of fluoride salts were prepared and coated as described above using the materials and amounts (in grams) as outlined in Table 12 below. These coating show sustained fluoride release. Films formed on 1 inch×1 inch (2.54 cm×2.54 cm) plastic slides were then evaluated for fluoride release (FR) as described above.

TABLE 12

|  | Ex. 41 | Ex. 42 | Ex. 43 | Ex. 44 | Ex. 45 | Ex. 46 | Ex. 47 |
|---|---|---|---|---|---|---|---|
| Eudragit S100 | 24 | 24 | 24 | 24 | 24 | 24 | 24 |
| EtOH | 110 | 110 | 110 | 110 | 110 | 110 | 110 |
| DI Water | 26 | 26 | 26 | 26 | 26 | 26 | 26 |
| Eudragit RS100 | 20 | 20 | 20 | 20 | 20 | 20 | 20 |
| Eudragit E100 | 0.3 | 0.3 | 0.3 | 0.3 | 0.3 | 0.3 | 0.3 |
| glycerin | 20 | 20 | 20 | 20 | 20 | 20 | 20 |
| CaF$_2$ | 0 | 0 | 0 | 0.5 | 0 | 0 | 0 |
| SrF$_2$ | 1.5 | 3.4 | 4.9 | 3.15 | 1.5 | 3.4 | 4.9 |
| CaHPO$_4$ | 0 | 0 | 0 | 0 | 0.5 | 0.5 | 0.5 |
| NaF | 2.25 | 1.0 | 0 | 2.25 | 2.25 | 1.0 | 0 |
| Cumulative FR 1 hr | 88.74 | 47.7 | 13.32 | 65.95 | 81.9 | 36.3 | 5.1 |
| Cumulative FR 4 hr | 105.8 | 73.1 | 73.1 | 84.4 | 87.8 | 45.4 | 45.4 |
| Cumulative FR 6 hr | 111.0 | 85.1 | 85.1 | 91.8 | 89.9 | 48.8 | 48.8 |
| Cumulative FR 24 hr | 121.3 | 116.3 | 116.3 | 111.8 | 104.9 | 81.7 | 81.7 |

Coating compositions containing sodium fluoride and various combinations metal chloride salts were prepared and coated as described above using the materials and amounts (in grams) as outlined in Table 14 below. Films formed on 1 inch×1 inch (2.54 cm×2.54 cm) plastic slides were then evaluated for fluoride release (FR) as described above.

TABLE 13

|  | Ex. 48 | Ex. 49 | Ex. 50 |
|---|---|---|---|
| Eudragit S100 | 13 | 13 | 13 |
| EtOH | 52 | 52 | 52 |
| DI Water | 12 | 12 | 12 |
| Eudragit RS100 | 10 | 10 | 10 |
| Eudragit E100 | 0.2 | 0 | 0 |
| glycerin | 12 | 10 | 10 |
| CaCl$_2$ | 1 | 0 | 0 |
| SrCl$_2$ | 0 | 0.6 | 0 |
| MgCl$_2$•6H2O | 0 | 0 | 0.6 |
| TCP | 0.5 | 0.4 | 0.4 |
| NaF | 2 | 2 | 2 |
| Cumulative FR 1 hr | 51.0 | 67.4 | 64.1 |
| Cumulative FR 4 hr | 62.3 | 69.6 | 66.5 |
| Cumulative FR 6 hr | 68.3 | 69.8 | 66.7 |
| Cumulative FR 24 hr | 79.8 | 70.1 | 67 |

Examples 51-55

Color Coatings

Coating compositions containing various pigments were prepared and coated as described above using the materials and amounts (in grams) as outlined in Table 14 below. Films formed on 1 inch×1 inch (2.54 cm×2.54 cm) plastic slides were then evaluated for set, feel and adhesion as described above as well as for appearance (color).

TABLE 14

|  | Ex. 51 | Ex. 52 | Ex. 53 | Ex. 54 | Ex. 55 |
|---|---|---|---|---|---|
| EUDRAGIT S100 | 15 | 15 | 15 | 15 | 15 |
| Ethanol | 60 | 60 | 60 | 60 | 52 |
| DI water | 15 | 15 | 15 | 15 | 13 |
| glycerol | 0.0 | 0.0 | 0.0 | 0.0 | 10 |
| TiO$_2$ | 1.0 | 0.0 | 0.0 | 0.0 | 1.0 |
| EUDRAGIT E100 | 0.0 | 0.0 | 0.0 | 0.0 | 0.15 |
| EUDRAGIT RS100 | 10 | 10 | 10 | 10 | 10 |
| Ultramarine Blues | 0.0 | 1.0 | 0.0 | 0.0 | 0.0 |
| Invisible blue | 0.0 | 0.0 | 0.536 | 0.033 | 0.10 |
| Film feel | hard | hard | hard | hard | hard |
| Set in water | yes | yes | yes | yes | yes |
| Appearance | white | blue | Clear/fluorescence | Clear/fluorescence | White/fluorescence |
| Film adhesion | good | good | good | good | good |

Examples 56-59 and Comparative Examples 23-25

Aqueous Coating Compositions with Various Cosolvents

Coating compositions were prepared and coated as described above using the materials and amounts (in grams) as outlined in Table 15 below. Coated films were evaluated for dissolution, set and adhesion as described above.

TABLE 15

|  | Ex. 56 | Ex. 57 | Ex. 58 | CE 23 | CE 24 | CE 25 | Ex. 59 |
|---|---|---|---|---|---|---|---|
| EUDRAGIT S100 | 2.25 | 2.25 | 2.25 | 2.25 | 2.25 | 2.25 | 2.25 |
| Ethanol | 9 | 0 | 0 | 0 | 0 | 0 | 0 |
| DI water | 2.25 | 2.25 | 2.25 | 2.25 | 2.25 | 2.25 | 2.25 |
| IPA | 0 | 9 | 0 | 0 | 0 | 0 | 0 |
| 1-propanol | 0 | 0 | 9 | 0 | 0 | 0 | 0 |
| THF | 0 | 0 | 0 | 9 | 0 | 0 | 0 |
| DMSO | 0 | 0 | 0 | 0 | 9 | 0 | 0 |
| Ionic liquid | 0 | 0 | 0 | 0 | 0 | 9 | 0 |
| Acetone | 0 | 0 | 0 | 0 | 0 | 0 | 9 |
| EUDRAGIT RS100 | 1.5 | 1.5 | 1.5 | 1.5 | 1.5 | 1.5 | 1.5 |
| Polymer dissolution | yes | yes | yes | no | no | no | yes |
| Set in water | yes | yes | yes | — | — | — | yes |
| adhesion | good | good | good | — | — | — | good |

Examples 60-70

Coating Composition Consistency

Coating compositions were prepared and coated as described above using the materials and amounts (in grams) as outlined in Table 16 below. The consistency numbers were measured with the method listed above described above and are reported as 1/32 inch (0.79 mm).

TABLE 16

Examples with consistency measurements

|  | Ex. 60 | Ex. 61 | Ex. 62 | Ex. 63 | Ex. 64 | Ex. 65 | Ex. 66 | Ex. 67 | Ex. 68 | Ex. 69 | Ex. 70 |
|---|---|---|---|---|---|---|---|---|---|---|---|
| EUDRAGIT S100 | 5 | 5 | 0 | 3 | 8.83 | 11.96 | 11.96 | 13.1 | 13.1 | 7 | 5 |
| EUDRAGIT L100-55 | 0 | 0 | 12.5 | 0 | 0 | 0 | 0 | 0 | 0 | 0 | 0 |
| Ethanol | 45 | 40 | 50 | 50 | 58.3 | 58.4 | 52.8 | 58.2 | 55.0 | 50 | 54.5 |
| DI water | 10 | 15 | 12 | 12 | 11.6 | 9.97 | 12.7 | 11.6 | 11.0 | 12 | 12 |
| glycerol | 0 | 0 | 0 | 0 | 9.32 | 9.97 | 12.7 | 9.32 | 13.2 | 0 | 0 |
| EUDRAGIT E100 | 0 | 0 | 0 | 0 | 0.15 | 0.175 | 0.225 | 0.2 | 0.15 | 0 | 0 |
| EUDRAGIT RS100 | 0 | 0 | 0 | 0 | 11.77 | 9.57 | 9.56 | 7.49 | 7.49 | 0 | 0 |
| EUDRAGIT RL100 | 40 | 40 | 20 | 34 | 0 | 0 | 0 | 0 | 0 | 30 | 28 |
| Xylitol | 0 | 0 | 5 | 1 | 0 | 0 | 0 | 0 | 0 | 1 | 0.5 |
| Setting in water | yes | yes | yes | yes | yes | yes | yes | yes | yes | yes | yes |
| consistency | 60 | 53 | 74 | 75 | 100 | 88 | 72 | 91 | 62 | 60 | 74 |

Example 48

Abrasion Resistance

The abrasion resistance on bovine teeth of coating composition of Ex 48 was determined as described above. Three replicate samples of coated teeth were soaked in 37° C. artificial saliva for either 3 hours or 24 hours and then subjected to brushing. The amount of coating removed after a specific number of brush strokes is reported in Table 17 below.

TABLE 17 coating brushing durability after stored in 37 C. artificial saliva for certain time (worn out %)

|  |  | 37 C. artificial saliva for 3 hrs | | | | 37 C. artificial saliva for 24 hrs | | | |
| --- | --- | --- | --- | --- | --- | --- | --- | --- | --- |
| strokes | Tooth# | 30 | 60 | 90 | 120 | 30 | 60 | 90 | 120 |
| Ex 48 | 1 | 0% | 10% | 50% | 90% | 0% | 10% | 50% | 90% |
|  | 2 | 0% | 10% | 10% | 50% | 0% | 20% | 50% | 90% |
|  | 3 | 0% | 10% | 10% | 10% | 0% | 10% | 10% | 30% |

Example 71

Coating Composition for Sensitivity Reduction

A coating composition suitable for reducing tooth sensitivity was prepared as described above using the materials and amounts (in grams) as outlined in Table 18 below.

TABLE 18

|  | Ex 71 |
| --- | --- |
| EUDRAGIT S100 | 12 |
| Ethanol | 51.7 |
| DI water | 12.5 |
| glycerol | 12.5 |
| EUDRAGIT RS100 | 11 |
| EUDRAGIT E100 | 0.3 |
| NaF | 3.0 |
| KNO$_4$ | 1.0 |
| mint flavor | 0.5 |
| SrF$_2$ | 0.4 |
| TCP | 0.5 |

The sensitivity reduction coating was painted on different dental appliances, restorative material and their combinations with tooth structures. These coatings were set into hard and slippery film on these substrates by exposing the coating to water or artificial saliva. Restorative substrates were in the form of cured disks (15 mm diameter by 1 mm thick prepared by placing the indicated restorative dental material in a stainless steel mold, flattening the material with a press and then light curing with a 3M ESPE S10 LED curing light (available from 3M Company, St Paul, Minn.). With the exception of the bovine tooth, all materials and articles used in this test are available from 3M Company, St Paul, Minn. The coatings were evaluated as to whether or not a coating was formed on the substrate and how the coating was felt by finger touch. The observations for these coated substrates are shown in Table 19 below.

TABLE 19

| Substrate Material | Coating Formed | Coating Feel |
| --- | --- | --- |
| 3M UNITEK orthodontic wire and bracket | Yes | Hard and slippery |
| Cured 3M ESPE KETAC Nano RMGI filling material | Yes | Hard and slippery |
| Cured 3M ESPE FILTEK Z250 composite filling material | Yes | Hard and slippery |
| 3M ESPE LAVA ULTIMATE crown | Yes | Hard and slippery |
| Cured 3M ESPE RelyX ultimate resin Cement | Yes | Hard and slippery |
| Cured 3M ESPE FILTEK bulk flowable composites | Yes | Hard and slippery |
| Bovine tooth cleaned with tooth brush | Yes | Hard and slippery |
| 3M ESPE stainless steel crown | Yes | Hard and slippery |
| 3M ESPE LAVA PLUS zirconia crown material | Yes | Hard and slippery |

An SEM image of a bovine tooth prepared and coated as described above was made to demonstrate that the coating composition outlined in Table 18 formed a physical barrier to block dentin tubules to reduce tooth sensitivity. The SEM image of the bovine tooth (FIG. 1) shows half of dentin tubules blocked by the coating on the left side as well as the open uncoated dentin tubules pm the right side.

Examples 72-80

Non-Aqueous Coating Compositions with Various Solvents

Coating compositions were prepared and coated and as described above using the materials and amounts (in grams) as outlined in Table 20 below. Coated films were evaluated for dissolution, set and adhesion as described above.

TABLE 20

|  | Ex 72 | Ex 73 | Ex 74 | Ex 75 | Ex 76 | Ex 77 | Ex 78 | Ex 79 | Ex 80 |
| --- | --- | --- | --- | --- | --- | --- | --- | --- | --- |
| EUDRAGIT S100 | 2.25 | 2.25 | 2.25 | 2.25 | 2.25 | 2.25 | 2.25 | 2.25 | 2.25 |
| Ethanol | 0 | 0 | 0 | 0 | 0 | 0 | 9 | 9 | 9 |
| THF | 0 | 0 | 0 | 0 | 0 | 0 | 0 | 0 | 2.25 |
| EtOAc | 0 | 0 | 0 | 0 | 2.25 | 4.25 | 0 | 0 | 0 |
| TEC | 0 | 0 | 2.25 | 4.25 | 0 | 2.25 | 0 | 0 | 0 |
| DMSO | 2.25 | 7 | 0 | 7 | 0 | 7 | 2.25 | 0 | 0 |
| Acetone | 9 | 4.24 | 9 | 0 | 9 | 0 | 0 | 0 | 0 |

TABLE 20-continued

|  | Ex 72 | Ex 73 | Ex 74 | Ex 75 | Ex 76 | Ex 77 | Ex 78 | Ex 79 | Ex 80 |
|---|---|---|---|---|---|---|---|---|---|
| Ionic Liquid | 0 | 0 | 0 | 0 | 0 | 0 | 0 | 2.25 | 0 |
| EUDRAGIT RS100 | 1.5 | 1.5 | 1.5 | 1.5 | 1.5 | 1.5 | 1.5 | 1.5 | 1.5 |
| Polymer dissolution | yes | yes | yes | yes | yes | yes | yes | yes | yes |
| Set in water | yes | yes | yes | yes | yes | yes | yes | yes | yes |
| adhesion | good | good | good | good | good | good | good | good | good |

What is claimed is:

1. An oral composition, comprising:
a solvent comprising water and a cosolvent chosen from lower alkyl alcohols, acetone and a combination thereof;
optionally a nonpolymeric active agent; and
a combination of polymers comprising at least one acidic copolymer comprising acidic acrylate monomeric units, acidic methacrylate monomeric units, or a combination thereof; and at least one neutral copolymer comprising neutral acrylate monomeric units, neutral methacrylate monomeric units, or a combination thereof;
wherein the oral composition comprises from about 6 to about 18 wt-% of water, from about 30 to about 80 wt-% of cosolvent, from about 15 to about 50 wt-% of the sum of the acidic and neutral acrylate and/or methacrylate copolymers, and the wt-% of each component is based on the total weight of the composition;
wherein the acidic and neutral acrylate and/or methacrylate copolymers are dissolved in the oral composition; and
wherein the oral composition is capable of forming a film on a surface when contacted with an aqueous solution.

2. The oral composition of claim 1, wherein the cosolvent is ethanol.

3. The oral composition of claim 1, wherein the oral composition comprises from about 8 to about 12 wt-% of water, and wherein the oral composition comprises from about 45 to about 60 wt-% of the cosolvent.

4. The oral composition of claim 1, wherein the oral composition is capable of forming the film in less than about 30 seconds after the oral composition is contacted with water.

5. The oral composition of claim 1, wherein the solvent further comprises at least one additional component chosen from isopropanol, propylene glycol, glycerin, low molecular weight polyethylene glycol, ethylene glycol based ester alcohols, and combinations thereof.

6. The oral composition of claim 1, wherein the molecular weight of the acidic acrylate and/or methacrylate copolymers is from about 5,000 to about 500,000, and wherein the molecular weight of the neutral acrylate and/or methacrylate copolymers is from about 10,000 to about 100,000.

7. The oral composition of claim 1, wherein the oral composition comprises from about 20 to about 48 wt-% of the sum of the acidic and neutral acrylate and/or methacrylate copolymers.

8. The oral composition of claim 1, wherein the film remains on at least 90% of the surface after brushing the surface for at least 5 strokes.

9. The oral composition of claim 1, wherein the optional nonpolymeric active agent provides a sustained fluoride release for at least 24 hours.

10. The oral composition of claim 1, wherein the optional nonpolymeric active agent comprises at least two different fluoride salts.

11. The oral composition of claim 1, wherein the optional nonpolymeric active agent is chosen from sodium fluoride, strontium fluoride, calcium fluoride, zinc fluoride, calcium chloride, calcium nitrate, calcium phosphates, calcium hydrogen phosphate, calcium dihydrogen phosphate, and combinations thereof.

12. An oral composition, comprising:
a solvent comprising water and a cosolvent chosen from lower alkyl alcohols, THF, DMSO, ionic liquid, TEC, ethyl acetate, acetone, and a combination thereof;
optionally a nonpolymeric active agent; and
a combination of polymers comprising at least one acidic copolymer comprising acidic acrylate monomeric units, acidic methacrylate monomeric units, or a combination thereof; at least one neutral copolymer comprising neutral acrylate monomeric units, neutral methacrylate monomeric units, or a combination thereof; and at least one basic copolymer comprising basic acrylate monomeric units, basic methacrylate monomeric units, or a combination thereof;
wherein the oral composition comprises from about 6 to about 18 wt-% of water, from about 30 to about 80 wt-% of the sum of water and the cosolvent, from about 15 to about 50 wt-% of the sum of the acidic and neutral acrylate and/or methacrylate copolymers, and from about 0 to about 1.0 wt-% of the at least one basic acrylate and/or methacrylate copolymer, and the wt-% of each component is based on the total weight of the composition;
wherein the acidic, basic, and neutral acrylate and/or methacrylate copolymers are dissolved in the oral composition; and
wherein the oral composition is capable of forming a film on a surface when contacted with an aqueous solution.

13. The oral composition of claim 12, wherein the weight ratio of the basic acrylate and/or methacrylate copolymers to the acidic acrylate and/or methacrylate polymers is from about 0 to about 1:10, and wherein the weight ratio of the basic acrylate and/or methacrylate copolymers to the acidic acrylate and/or methacrylate polymers is from about 1:100 to about 1:15.

14. The oral composition of claim 12, wherein the molecular weight of the at least one basic acrylate and/or methacrylate copolymer is from about 10,000 to about 100,000.

15. The oral composition of claim 1, wherein the optional nonpolymeric active agent is selected from whitening agents, anticaries agents, fluoride-delivery agents, anti-gingivitis agents, tartar control agents, antiplaque agents, periodontal actives, breath freshening agents, malodor control agents, tooth desensitizers, salivary stimulants, flavors, biofilm disruptors, antimicrobials, anesthetic agent, pain killers, stain removal agents, coloring agents, remineralization agents, calculus-softening agents, and combinations thereof, and wherein the active agent is a fluoride composition.

16. A method of delivering an oral composition to a dental structure comprising:
   providing an oral composition according to claim 1;
   applying the oral composition to the dental structure; and
   contacting the oral composition with an aqueous solution, thereby forming a polymeric film on the dental structure.

* * * * *

UNITED STATES PATENT AND TRADEMARK OFFICE
CERTIFICATE OF CORRECTION

PATENT NO. : 10,064,802 B2
APPLICATION NO. : 14/917431
DATED : September 4, 2018
INVENTOR(S) : Yizhong Wang Page 1 of 2

It is certified that error appears in the above-identified patent and that said Letters Patent is hereby corrected as shown below:

In the Specification

Column 2
Line 7, Delete "derivates" and insert -- derivatives --, therefor.

Column 5
Lines 14-15, Delete "Damstadt," and insert -- Darmstadt, --, therefor.

Column 5
Line 16, Delete "Damstadt," and insert -- Darmstadt, --, therefor.

Column 5
Line 17, Delete "Damstadt," and insert -- Darmstadt, --, therefor.

Column 5
Line 53, Delete "trimethylopropane" and insert -- trimethylolpropane --, therefor.

Column 5
Lines 60-61, Delete "Damstadt," and insert -- Darmstadt, --, therefor.

Column 5
Line 62, Delete "Damstadt," and insert -- Darmstadt, --, therefor.

Column 9
Line 30, Delete "bisguanides," and insert -- biguanides, --, therefor.

Column 10
Line 30, Delete "flucinolone" and insert -- fluocinolone --, therefor.

Signed and Sealed this
Twenty-third Day of April, 2019

Andrei Iancu
*Director of the United States Patent and Trademark Office*

Column 11
Lines 13-14, Delete "monofluorophosphates," and insert -- monofluorophosphate, --, therefor.

Column 16
Line 18 (approx.), After "composition" insert -- . --.

Columns 15-16
Line 35 (approx.), Delete "Pasippany," and insert -- Parsippany, --, therefor.

Columns 15-16
Line 47, Delete "acic" and insert -- acid --, therefor.

Columns 17-18
Line 39 (approx.), Delete "Pasippany," and insert -- Parsippany, --, therefor.

Column 17
Line 55, Delete "FlacTek, Inc.," and insert -- FlackTek, --, therefor.

Column 20
Line 16 (approx.), Delete "Solution," and insert -- Solutions, --, therefor.

Column 20
Line 16 (approx.), Delete "Greenbay" and insert -- Green Bay --, therefor.

Column 20
Line 18 (approx.), Delete "gental" and insert -- dental --, therefor.

Column 20
Line 43 (approx.), After "microscope" insert -- . --.